US010646553B2

(12) United States Patent
Han et al.

(10) Patent No.: US 10,646,553 B2
(45) Date of Patent: May 12, 2020

(54) USE OF RECOMBINANT HUMAN CALCINEURIN B SUBUNIT

(71) Applicant: HAIKOU QILI PHARMACEUTICAL CO., LTD., Haikou, Hainan (CN)

(72) Inventors: Kesheng Han, Hainan (CN); Jian Fu, Hainan (CN); Zongwen Huang, Hainan (CN); Shuhong Tian, Hainan (CN); Lifang Han, Hainan (CN)

(73) Assignee: HAIKOU QILI PHARMACEUTICAL CO., LTD., Haikou, Hainan (CN)

( * ) Notice: Subject to any disclaimer, the term of this patent is extended or adjusted under 35 U.S.C. 154(b) by 0 days.

(21) Appl. No.: 16/020,363

(22) Filed: Jun. 27, 2018

(65) Prior Publication Data

US 2018/0311320 A1 Nov. 1, 2018

Related U.S. Application Data

(63) Continuation of application No. PCT/CN2016/110744, filed on Dec. 19, 2016.

(30) Foreign Application Priority Data

Dec. 30, 2015 (CN) .......................... 2015 1 1021735

(51) Int. Cl.
| | |
|---|---|
| *A61K 38/46* | (2006.01) |
| *A61K 9/00* | (2006.01) |
| *A61P 35/04* | (2006.01) |
| *A61K 9/08* | (2006.01) |

(52) U.S. Cl.
CPC .......... *A61K 38/465* (2013.01); *A61K 9/0019* (2013.01); *A61K 9/08* (2013.01); *A61P 35/04* (2018.01); *C12Y 301/03016* (2013.01)

(58) Field of Classification Search
CPC ...... A61K 38/465; A61K 9/0019; A61K 9/08; A61P 35/04; C12Y 301/03016
See application file for complete search history.

(56) References Cited

U.S. PATENT DOCUMENTS 7,026,118 B1 * 4/2006 Wei .......................... C12N 9/16
435/6.16

FOREIGN PATENT DOCUMENTS

| CN | 1245720 A | 3/2000 |
|---|---|---|
| CN | 1351161 A | 5/2002 |
| CN | 105435216 A | 3/2016 |

OTHER PUBLICATIONS

Qun Wei, Studies of Calcineurin B Subunit From Genetic Engineering for Use in Medicine, Drug Development Research 56:40-43 (2002).*
Zhenyi Su, The Multiple Mechanisms of Anti-Tumor function of Calcineurin B Subunit, t. J J Mol Transl Med. 2015, 1(1): 003.*
Mechanisms of carcinogenesis, section 3, published 2008, International agency for research on cancer.*
International Search Report for PCT/CN2016/110744 dated Mar. 24, 2017, ISA/CN.
SIPO First Office Action corresponding to Application No. 201511021735.3; Issued date of May 18, 2016.
Ma, Xiangtao et al., "Research on Calcineurin signal Transduction Pathways and Mechanisms Involved in Gastric Cancer" Chinese Journal of Gastrointestinal Sugery, vol. 9. No. 4, Jul. 31, 2006. pp. 352-353.
Liu. C. et al., "The RCAN1 inhibits Nf-kB and suppresses lymphoma growth in mice" Cell Death and Disease, vol. 6, Oct. 22, 2015. e1929.
Liu Dong et al., "Research progress on the role of calcineurin in tumor bone metastasis" Shaanxi medical journal, vol. 38, No. 11, Nov. 30, 2009. pp. 1527-1529.
Wei Qun et al.,"Study on immune properties and functions of calcineurin and its subunits" Chinese Biochemical Journal,vol. 9, No. 2, Apr. 30, 1993. pp. 240-243.

* cited by examiner

*Primary Examiner* — Rachael E Bredefeld
*Assistant Examiner* — Erinne R Dabkowski
(74) *Attorney, Agent, or Firm* — Yue (Robert) Xu; Apex Attorneys at Law, LLP (57) ABSTRACT

Provided is a use of a recombinant human calcineurin B subunit (rhCNB) in the preparation of a medicine for killing and/or inhibiting the gastric cancer.

9 Claims, 3 Drawing Sheets

Figure 1

Note: "X" indicates that the animal died before the end of the recovery period.

USE OF RECOMBINANT HUMAN CALCINEURIN B SUBUNIT

This application is a continuation application of international patent application No. PCT/CN2016/110744, filed on Dec. 19, 2016, which claims the priority of Chinese Patent Application No. 201511021735.3, filed on Dec. 30, 2015, the disclosures of each of which are incorporated herein by reference in their entirety.

FIELD

The present invention relates to the field of proteins, and particularly relates to the use of a recombinant human calcineurin B subunit.

BACKGROUND

Calcineurin (CN) is the only protein phosphatase currently known to be dependent on $Ca^{2+}$/CaM (calmodulin) and consists of A and B subunits in a 1:1 ratio. The A subunit (CNA) is a catalytic subunit, and the B subunit (CNB) is a regulatory subunit. CN plays an important role in the immune activation pathway and is a key enzyme for T cell activation. CN, as a macromolecular enzyme protein, is easily inactivated and unstable. CNB, as a regulatory subunit of this enzyme, can promote the activity of CNA, and have a relatively small molecular weight and stable properties. Studies have shown that CNB can stimulate the proliferation of T cells and NK cells, improve immune functions such as enhancing the activity of NK cells, enhancing the phagocytic ability of macrophages, and the like.

However, up to date, there is no related report about the killing or inhibiting effect of rhCNB on the gastric cancer cell MGC-803.

SUMMARY

In view of above, the present invention provides use of a recombinant human calcineurin B subunit. The present invention uses IVIS Kinetics (a small animal live imaging system) to study the therapeutic effect of rhCNB for injection on BALB/c nude mice bearing human gastric cancer cell MGC-803 carcinoma in situ. The present invention further investigates the killing and/or inhibiting effects of rhCNB for injection on specific types of tumor cells, and explores the relationship between the time-effect and dose-effect of the subject for producing pharmacodynamic effects, thus providing a basis for the effectiveness and other toxicologically related tests of the drug.

In order to achieve the above objects of the present invention, the present invention provides the following technical solutions:

The present invention provides a use of rhCNB in the preparation of a medicine for killing and/or inhibiting the gastric cancer cell MGC-803.

In some specific embodiments of the present invention, in the use of rhCNB in the preparation of a medicine for killing and/or inhibiting the gastric cancer cell MGC-803, the rhCNB is administrated at a dose of not less than 10 mg/kg.

In some specific embodiments of the present invention, in the use of rhCNB in the preparation of a medicine for killing and/or inhibiting the gastric cancer cell MGC-803, the rhCNB is administrated at a dose between 10 mg/kg and 160 mg/kg.

In some specific embodiments of the present invention, in the use of rhCNB in the preparation of a medicine for killing and/or inhibiting the gastric cancer cell MGC-803, the rhCNB is administrated at a concentration between 0.5 mg/mL and 2 mg/mL.

In some specific embodiments of the present invention, in the use of rhCNB in the preparation of a medicine for killing and/or inhibiting the gastric cancer cell MGC-803, the rhCNB is administrated via intravenous injection once daily for 15 consecutive days, or at a first administration dose of 10 mg/kg, followed by progressively increasing dose by one fold every 3 days, which are 10 mg/kg, 20 mg/kg, 40 mg/kg, 80 mg/kg, and 160 mg/kg successively.

The present invention also provides a use of rhCNB in the preparation of a medicine for treating BALB/c nude mice bearing transplantation tumor of human gastric cancer cell MGC-803 carcinoma in situ.

In some specific embodiments of the present invention, in the use of rhCNB in the preparation of a medicine for treating BALB/c nude mice bearing transplantation tumor of human gastric cancer cell MGC-803 carcinoma in situ, the rhCNB is administrated at a dose of not less than 10 mg/kg.

In some specific embodiments of the present invention, in the use of rhCNB in the preparation of a medicine for treating BALB/c nude mice bearing transplantation tumor of human gastric cancer cell MGC-803 carcinoma in situ, the rhCNB is administrated at a dose between 10 mg/kg and 160 mg/kg.

In some specific embodiments of the present invention, in the use of rhCNB in the preparation of a medicine for treating BALB/c nude mice bearing transplantation tumor of human gastric cancer cell MGC-803 carcinoma in situ, the rhCNB is administrated at a concentration between 0.5 mg/mL and 2 mg/mL.

In some specific embodiments of the present invention, in the use of rhCNB in the preparation of a medicine for treating BALB/c nude mice bearing transplantation tumor of human gastric cancer cell MGC-803 carcinoma in situ, the rhCNB is administrated via intravenous injection once daily for 15 consecutive days, or at a first administration dose of 10 mg/kg, followed by progressively increasing dose by one fold every 3 days, which are 10 mg/kg, 20 mg/kg, 40 mg/kg, 80 mg/kg, and 160 mg/kg successively.

During the experiment, except for the animals in the positive control high-dose group administrated with cisplatin for injection, there is no significant difference in the general symptoms and body weight of other animals as compared with the vehicle control group. After 3 and 6 continuous administrations, each administration group has no statistical significance as compared with the vehicle control group, with all p value >0.05. The test results show that, after 6 continuous administrations, the proliferation of tumor cells in each administration group of various doses of rhCNB for injection and the positive control administration groups is well controlled, but there is no statistical significance as compared with the vehicle control group, with all p value >0.05. The results of administration for 9 consecutive days show that the administration groups G (high-dose group), Z (medium-dose group), D (low-dose group), DZ (progressively increasing-dose group) and the positive control administration groups SD and X all show statistical significance on the control of tumor cell proliferation as compared with the vehicle control group, with p<0.01. The positive control administration group B shows statistical significance as compared with the vehicle control group, with p<0.05. The test results of administration for 12 consecutive days and 15 consecutive days show that the administration groups G (high-dose group), Z (medium-dose group), D (low-dose group), DZ (progressively increasing-dose group) and the positive control administration groups B, SD and X all show extremely significant differences on the control of tumor cell proliferation as compared with the vehicle control group, with p<0.001. The test results on the 7th day after the last administration show that, the administration groups G (high-dose group), Z (medium-dose group), D (low-dose group), DZ (progressively increasing-dose group) and the positive control administration group B all show extremely significant differences on the control of tumor cell proliferation as compared with the vehicle control group, with p<0.001. The administration groups SD and X show significant differences, with p<0.01.

In the therapeutic effect of rhCNB for injection on BALB/c nude mice bearing transplantation tumor of human gastric cancer cell MGC-803 carcinoma in situ, the tumor is effectively treated after 6 continuous administrations (as compared with the vehicle control group, p<0.05), and can be effectively controlled throughout the administration. One week after drug withdrawal, there is still a continuous and effective therapeutic effect on tumor control (as compared with the vehicle control group, p<0.001), which is superior to the positive controls cisplatin for injection and hydroxycamptothecin for injection, and is comparable to the recombinant human interleukin-2 for injection.

DESCRIPTION OF THE DRAWINGS

In order to more clearly illustrate the technical solutions in the Examples of the present invention or in the prior art, the drawings needed to be used in the description of the Examples or the prior art will be briefly introduced below.

DETAILED DESCRIPTION OF EMBODIMENTS

The present invention discloses the use of a recombinant human calcineurin B subunit, which can be achieved by those skilled in the art by appropriately improving the process parameters in light of the disclosure. In particular, it should be noted that, all similar substitutions and modifications will be apparent to those skilled in the art, and are all considered to be included in the present invention. The method and use of the present invention have been described by preferred examples, and it is obvious that related ones can make alterations or appropriate changes and combinations to the method and use described herein so as to implement and use the techniques of the present invention without departing from the content, spirit and scope of the present invention.

According to the present invention, the recombinant human calcineurin B subunit or its functional variant or fragment can be used to treat cancer in a subject in need, preferably gastric cancer. The term "treat" refers to killing or inhibiting the proliferation of cancer cells. The term "functional variant or fragment of the recombinant human calcineurin B subunit" refers to a peptide having the same functions as wild-type human calcineurin B subunit but a different amino acid sequence.

In one embodiment of the present invention, the cancer is derived from human gastric cancer cell MGC-803.

In one embodiment of the present invention, according to the "Technical Guidelines for Non-Clinical Studies of Cytotoxic Antitumor Drugs" and "Guidelines for Pharmacodynamics of Antitumor Drugs", IVIS Kinetics (a small animal live imaging system) was used to dynamically analyze the therapeutic effect of rhCNB for injection on the BALB/c nude mice bearing the human gastric cancer cell MGC-803 carcinoma in situ. Firstly, a BALB/c nude mouse model bearing subcutaneous transplantation tumor of human gastric cancer cell MGC-803 was established, and then a BALB/c nude mouse model bearing transplantation tumor in situ of human gastric cancer cell MGC-803 was established. 90 nude mice modeled successfully were taken and evenly divided into 9 administration groups according to the values of bioluminescence, including: high-dose group of rhCNB for injection (administration dose, 40 mg/kg; administration concentration, 2 mg/mL), medium-dose group of rhCNB for injection (administration dose, 20 mg/kg; administration concentration, 1 mg/mL), low-dose group of rhCNB for injection (administration dose, 10 mg/kg; administration concentration, 0.5 mg/mL), progressively increasing-dose group of rhCNB for injection (with the first administration dose of 10 mg/kg, followed by increasing dose by one fold every 3 days, which are 10 mg/kg, 20 mg/kg, 40 mg/kg, 80 mg/kg, and 160 mg/kg successively), positive control administration group of recombinant human interleukin-2 for injection (administration dose, 164,000 IU/kg; administration concentration, 8200 IU/mL), positive control high-dose administration group of cisplatin for injection (5 mg/kg; administration concentration, 0.25 mg/mL), positive control low-dose administration group of cisplatin for injection (1 mg/kg; administration concentration, 0.05 mg/mL), positive control administration group of hydroxycamptothecin for injection (2 mg/kg; administration concentration, 0.1 mg/mL) and vehicle control group. Each experimental group is administered once daily for 15 consecutive days, except that the positive control high-dose administration group of cisplatin for injection is administered for 5 days. Animals were observed for general symptoms before and after each administration. Animals were examined once using Caliper IVIS Kinetics (small animal live imaging system) before the first administration (on the administration day), every other 3 days after the first administration and on the 7th day after the last administration, respectively, and body weight was measured before each examination. At the end of the last examination, animals were sacrificed and roughly necropsied, and organs inoculated with tumor (including tumor tissues) were removed for pathological examination and immunohistochemical assay of apoptosis.

Results

During the experiment, except for the animals in the positive control high-dose group administrated with cisplatin for injection, there is no significant difference in the general symptoms and body weight of other animals as compared with the vehicle control group. After 3 and 6 continuous administrations, each administration group has no statistical significance as compared with the vehicle control group, with all p value >0.05. The test results show that, after 6 continuous administrations, the proliferation of tumor cells in each administration group with various doses of rhCNB for injection and the positive control administration groups is well controlled, but there is no statistical significance as compared with the vehicle control group, with all p value >0.05. The results of administration for 9 consecutive days show that, the administration groups G (high-dose group), Z (medium-dose group), D (low-dose group), DZ (progressively increasing-dose group) and the positive control administration groups SD and X, all show statistical significance on the control of tumor cell proliferation as compared with the vehicle control group, with $p<0.01$. The positive control administration group B shows statistical significance as compared with the vehicle control group, with $p<0.05$. The test results of administration for 12 consecutive days and 15 consecutive days show that, the administration groups G (high-dose group), Z (medium-dose group), D (low-dose group), DZ (progressively increasing-dose group), and the positive control administration groups B, SD and X, all show extremely significant differences on the control of tumor cell proliferation as compared with the vehicle control group, with $p<0.001$. The test results on the 7th day after the last administration show that, the administration groups G (high-dose group), Z (medium-dose group), D (low-dose group), DZ (progressively increasing-dose group) and the positive control administration group B all show extremely significant differences on the control of tumor cell proliferation as compared with the vehicle control group, with $p<0.001$. The administration groups SD and X show significant differences, with $p<0.01$.

Conclusions

In the therapeutic effect of rhCNB for injection on BALB/c nude mice bearing transplantation tumor of human gastric cancer cell MGC-803 carcinoma in situ, the tumor is effectively treated after 6 continuous administrations (as compared with the vehicle control group, $p<0.05$), and can be effectively controlled throughout the administration. One week after drug withdrawal, there is still a continuous and effective therapeutic effect on tumor control (as compared with the vehicle control group, $p<0.001$), which is superior to the positive controls cisplatin for injection and hydroxycamptothecin for injection, and is comparable to the recombinant human interleukin-2 for injection.

The raw materials and reagents used in the present invention are all commercially available.

Tumor cell line: the luc bioluminescence labeled gastric cancer cell line MGC-803 is purchased from Sinochrome, Shanghai.

Cell culture medium: Gibco RPMI1640 cell culture medium (500 mL/bottle)

Fetal bovine serum: MP fetal bovine serum (500 mL/bottle)

Cell digesting solution: Gibco cell digesting solution

Substrate: Caliper firefly D-luciferin potassium salt

Anaesthetic: isoflurane

Experimental animals: BALB/c nude mice are purchased from Guangdong Medical Laboratory Animal Center, certification No. 4400720001367.

The present invention will be further elaborated below in combination with the examples:

Example 1

Establishment Model of BALB/c Nude Mice Bearing Subcutaneous Transplantation Tumor of Human Gastric Cancer Cell MGC-803

Human gastric cancer cell MGC-803 was routinely cultured in vitro, digested, centrifuged, and then prepared into a cell suspension with a concentration of approximately $1\times10^7$ cells/mL. The cells were inoculated subcutaneously into the right armpit of mice at an amount of 0.2 mL/mouse.

Example 2

Establishment Model of BALB/c Nude Mice Bearing Transplantation Tumor In Situ of Human Gastric Cancer Cell MGC-803

Well-grown subcutaneously transplanted tumors were removed and cut into tumor tissue blocks with a size of approximately $2\times2\times1$ mm for use. Animals to be inoculated were feed 12 hours before surgical operation and subjected to gas anesthesia with isoflurane. The anaesthetized animals were placed in supine position. The skin 2~5 mm below the xiphoid process was cut horizontally layer-by-layer on the left side to give an opening of about 1 cm. Stomach was pull out gently using a pincette and exposed. The tumor tissue block was placed above the side near the pylorus of greater curvature of stomach of the nude mice with surgical suture #1 by "purse-string suture", so that the tumor tissue block was wrapped therein. The skin was sutured layer by layer and disinfected by Entoiodine, and then the animals were returned back to the cage for normal feeding. 7 days after surgery, the animals were examined using the small animal live imaging system, grouped, and administrated.

Example 3 Animal Grouping 90 inoculated nude mice were taken and randomly divided into 9 groups based on the detected bioluminescence data, that is, high-dose group of rhCNB for injection, medium-dose group of rhCNB for injection, low-dose group of rhCNB for injection, progressively increasing-dose group of rhCNB for injection, positive control administration group of recombinant human interleukin-2 for injection, positive control high-dose administration group of cisplatin for injection, positive control low-dose administration group of cisplatin for injection, positive control administration group of hydroxycamptothecin for injection and vehicle control group, 10 mice per group.

Example 4 Dose Design 1.2.4.1 Dose Design of the Test Sample rhCNB for Injection Referring to "high-, medium- and low-dose treatment groups are set in generally 4:2:1 for the treatment groups" in the "Guidelines for Pharmacodynamics of Antitumor Drugs", and "high-dose should not exceed the maximum tolerance dose of the test substance" in the "Technical Guidelines for Non-Clinical Studies of Cytotoxic Antitumor Drugs". A dose of 60 mg/day was intended to be used during the first clinical treatment course, and an increasing dose was intended to be used during the second, third, and fourth clinical treatment courses. Therefore, a total of 4 administration groups were set for the test sample rhCNB for injection, that is, the high-dose group of the test sample, the medium-dose group of the test sample, the low-dose group of the test sample and the progressively increasing-dose group of the test sample. The dose and concentration for administration were shown in Table 1.

1.2.4.2 Dose Design of Positive Drug 1.2.4.2.1 Dose Design of the Positive Drug Recombinant Human Interleukin-2 for Injection According to the instructions for the recombinant human interleukin-2 for injection, the common dose for clinical administration is 100,000-800,000 IU/time, once daily. According to the average human body weight of 60 kg, the dose for administration is calculated to be 800,000 IU÷6013≈300 IU/kg, which is converted into an equivalent dose of 13,300 IU/kg×12.33≈164,000 IU/kg for mice, and the concentration for administration is 8,200 IU/mL.

1.2.4.2.2 Dose Design of the Positive Drug Cisplatin for Injection

According to the descriptions in the instructions for cisplatin for injection, the general clinical daily dose for administration is 15-20 mg/m$^2$ of body surface area, with an administration for 5 consecutive days weekly. The average human body surface area is 1.62 m$^2$, that is, the clinical dose for administration is 15 mg/m$^2$×1.62 m$^2$=24.3 mg, and according to the average human body weight of 60 kg, the dose for administration is calculated to be 24.3 mg÷60=0.405 mg/kg, which is converted into an equivalent dose of 0.405 mg/kg×12.33≈5 mg/kg for mice. The concentration of high dose for administration is 0.25 mg/mL. Considering the administration for 15 consecutive days may cause the death of animal, a low-dose group is further set with a dose for administration of 1 mg/kg and a concentration for administration of 0.05 mg/mL.

1.2.4.2.3 Dose Design of the Positive Drug Hydroxycamptothecin for Injection

According to the descriptions in the instructions for hydroxycamptothecin for injection, the general clinical daily dose for administration is 4-6 mg/time, once daily, for 15-30 days, as one treatment course. According to the average human body weight of 60 kg, the dose for administration is calculated to be 6 mg÷60=0.1 mg/kg, which is converted into an equivalent dose of 0.1 mg/kg×12.33≈1.23 mg/kg for mice. The dose for administration is set to be 2 mg/kg with a concentration for administration of 0.1 mg/mL in this experiment.

Example 5

1.2.5 Route for Administration

The route for administration was by tail vein injection.

1.2.6 Administration Volume: 20 mL/Kg 1.2.7 Administration Time Period/Frequency The time period and frequency for administration of the test sample rhCNB for injection were designed based on the time and frequency intended to be used clinically, and the administration time period and frequency of the positive control group were designed based on the time period and frequency used clinically.

The high-, medium-, low-dose groups and progressively increasing-dose group of the test sample were administered once daily for 15 consecutive days;

the vehicle control group was administered once daily for 15 consecutive days;

the positive drug administration group of interleukin-2 for injection was administered once daily for 15 consecutive days;

the positive drug high dose administration group of cisplatin for injection was administered once daily for 5 consecutive days;

the positive drug low dose administration group of cisplatin for injection was administered once daily for 15 consecutive days;

the positive drug administration group of hydroxycamptothecin for injection was administered once daily for 15 consecutive days.

1.2.8 Detection Index 1.2.8.1 Symptom Observation

Animals were observed for the general symptoms before and after administration, and the observation indexes mainly included: whether the eating is normal, whether the water drinking is normal, whether the appearance of feces is normal, whether the appearance of urine is normal, whether the daily activities are normal, whether the breathing is normal, whether the heartbeat is normal, whether there is secreta in the eyes, nose and mouth, and body weight and the like.

1.2.8.2 Body Weight and Bioluminescence Detection

Animals were detected once using Caliper IVIS Kinetics small animal live imaging system at the following time point: before the first administration (on the administration day), every other 3 days after the first administration, and on the 7th day after the last administration, respectively. The body weight was measured before each detection. A substrate solution (with a concentration of 15 mg/mL) was injected intraperitoneally according to 0.1 mL/10 g body weight and a bioluminescence detection was performed 10~15 min after injection.

TABLE 1

Administration dose and schedule for each experimental group

| Group | Dose (concentration) schedule for administration | | | | |
|---|---|---|---|---|---|
| | d 1-d 3 | d 4-d 6 | d 7-d 9 | d 10-d 12 | d 13-d 15 |
| Progressively increasing dose group | 10 mg/kg (0.5 mg/mL) | 20 mg/kg (1 mg/mL) | 40 mg/kg (2 mg/mL) | 80 mg/kg (4 mg/mL) | 160 mg/kg (8 mg/mL) |
| Low-dose group | 10 mg/kg (0.5 mg/mL) | 10 mg/kg (0.5 mg/mL) | 10 mg/kg (0.5 mg/mL) | 10 mg/kg (0.5 mg/mL) | 10 mg/kg (0.5 mg/mL) |
| Medium-dose group | 20 mg/kg (1 mg/mL) | 20 mg/kg (1 mg/mL) | 20 mg/kg (1 mg/mL) | 20 mg/kg (1 mg/mL) | 20 mg/kg (1 mg/mL) |
| High-dose group | 40 mg/kg (2 mg/mL) | 40 mg/kg (2 mg/mL) | 40 mg/kg (2 mg/mL) | 40 mg/kg (2 mg/mL) | 40 mg/kg (2 mg/mL) |

TABLE 1-continued

Administration dose and schedule for each experimental group

| Group | d 1-d 3 | d 4-d 6 | d 7-d 9 | d 10-d 12 | d 13-d 15 |
|---|---|---|---|---|---|
| Positive drug administration group of recombinant human interleukin-2 | 164,000 IU/kg (8,200 IU/mL) | 164,000 IU/kg (8,200 IU/mL) | 164,000 IU/kg (8,200 IU/mL) | 164,000 IU/kg (8,200 IU/mL) | 164,000 IU/kg (8,200 IU/mL) |
| positive drug high-dose control group of cisplatin | 5 mg/kg (0.25 mg/mL) | 5 mg/kg (0.25 mg/mL) | 5 mg/kg (0.25 mg/mL) | 5 mg/kg (0.25 mg/mL) | 5 mg/kg (0.25 mg/mL) |
| positive drug low-dose control group of cisplatin | 1 mg/kg (0.05 mg/mL) | 1 mg/kg (0.05 mg/mL) | 1 mg/kg (0.05 mg/mL) | 1 mg/kg (0.05 mg/mL) | 1 mg/kg (0.05 mg/mL) |
| Positive drug control group of hydroxycamptothecin | 2 mg/kg (0.1 mg/mL) | 2 mg/kg (0.1 mg/mL) | 2 mg/kg (0.1 mg/mL) | 2 mg/kg (0.1 mg/mL) | 2 mg/kg (0.1 mg/mL) |
| Vehicle control group | 0.9% (g/mL) Sodium chloride injection was administrated in the same volume (20 mL/kg). | | | | |

1.2.8.3 Statistical Analysis

The data obtained from the experiments were statistically analyzed using SPSS analysis software, and the significance of difference between the administration groups and the vehicle control group, and among each administration group was compared.

Example 6 Experimental Results

2.1 Observation of General Symptoms

Animals were observed for the general symptoms before and after administration. Except for the positive control high-dose administration group of cisplatin for injection, there was no significant difference in the symptoms such as drinking water, appearance of faeces, appearance of urine, daily activities, breathing, heartbeat, secreta of eyes, nose and mouth of the animals in each remaining administration group as compared with the vehicle control group. In addition, the food intake of animals in each experimental group was decreased, mainly possibly due to the tumors in stomach which affected the digestive function of the animals.

2.2 Body Weight

Animals were measured for body weight before the first administration (on the administration day), every other 3 days after the first administration, and on the 7th day after the last administration, respectively. Except that there was significant difference in the body weight of the animals in the positive control high-dose administration group of cisplatin for injection as compared with the vehicle control group ($p<0.05$), there was no significant difference in the body weight of the each remaining administration group as compared with the vehicle control group, with $p>0.05$.

2.3 Bioluminescence Detection

Bioluminescence detection was performed using a Caliper IVIS small animal live imaging system before the first administration (on the administration day), every other 3 days after the first administration, and on the 7th day after the last administration, respectively. The detection results were shown in FIG. 1, FIG. 2 and Table 2.

Figure 1:
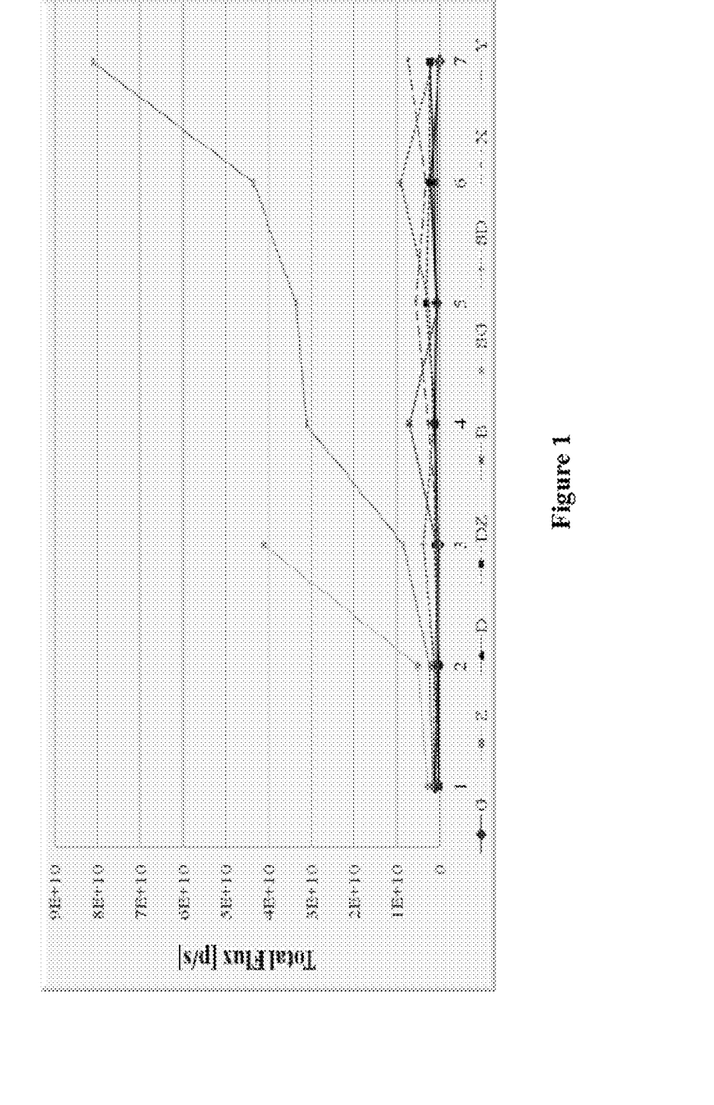
FIG. 1 shows the detected bioluminescence data ($\bar{x}$) for tumors in each experimental group, wherein "1~7" in the horizontal coordinates indicate "before administration, the 3th, 6th, 9th, 12th, 15th day after the first administration, and the 7th day during the recovery period after the last administration", respectively; "G, high-dose group (40 mg/kg) of rhCNB for injection", "Z, medium-dose group (20 mg/kg) of rhCNB for injection", "D, low-dose group (10 mg/kg) of rhCNB for injection", "DZ, progressively increasing-dose group of rhCNB for injection (10 mg/kg→20 mg/kg→40 mg/kg→80 mg/kg→160 mg/kg; with 10 mg/kg as the initial dose, followed by increasing one dose after administration for 3 consecutive days, and so forth)"; and the vertical coordinate is the detected bioluminescence intensity.

According to the data shown in FIG. 1, it can be seen that during the administration and recovery period, except for the positive control high-dose administration group of cisplatin for injection and the vehicle control group, the number of surviving tumor cells in the each remaining administration group fluctuates within a small range (<1E+10). Among them, the positive control high-dose administration group of cisplatin for injection shows a sharp increase in detection data after the 6th day administration, which is similar to that occurs in the experiment of human liver cancer cell Bel-7402 carcinoma in situ. However, when the solid tumor was touched, its volume was found not to significantly increase. After 9 continuous administrations, except for the positive control high-dose administration group of cisplatin for injection and the vehicle control group, the number of tumor cells proliferated in the each remaining administration group was significantly less than that of the vehicle control group.

TABLE 2

Analysis of p value and significance of difference of each experimental group during different administration periods

| Group | d0 | d3 | d6 | d9 | d12 | d15 | d21 |
|---|---|---|---|---|---|---|---|
| G | 1.000 (10) | .665 (10) | .988 (10) | .001** (10) | .000$^\Delta$ (10) | .000$^\Delta$ (10) | .000$^\Delta$ (9) |
| Z | .618 (10) | .975 (10) | .990 (10) | .001** (10) | .000$^\Delta$ (10) | .000$^\Delta$ (10) | .000$^\Delta$ (9) |
| D | .571 (10) | .483 (10) | .993 (10) | .001** (10) | .000$^\Delta$ (10) | .000$^\Delta$ (9) | .000$^\Delta$ (10) |
| DZ | .801 (10) | .695 (10) | .995 (10) | .001** (9) | .000$^\Delta$ (9) | .000$^\Delta$ (8) | .000$^\Delta$ (8) |
| B | .653 (10) | .622 (10) | .995 (8) | .015* (8) | .000$^\Delta$ (7) | .000$^\Delta$ (7) | .000$^\Delta$ (7) |
| SG | .833 (10) | .382 (10) | .058 (10) | — | — | — | — |
| SD | 1.000 (10) | .981 (10) | 1.000 (10) | .001** (10) | .000$^\Delta$ (10) | .000$^\Delta$ (9) | .003** (4) |
| X | .982 (10) | .852 (10) | .991 (9) | .002** (9) | .000$^\Delta$ (9) | .000$^\Delta$ (9) | .001** (7) |
| Y | — (10) | — (10) | — (10) | — (10) | — (8) | — (8) | — (6) |

Note:
The number in the parentheses "( )" is the number of surviving animals; G, high-dose administration group of rhCNB for injection; Z, medium-dose administration group of rhCNB for injection; D, low-dose administration group of rhCNB for injection; DZ, progressively increasing-dose administration group of rhCNB for injection; SG, positive control drug high-dose administration group of cisplatin for injection; SD, positive control drug low-dose administration group of cisplatin for injection; B, positive control drug administration group of interleukin-2 for injection; X, positive control drug administration group of hydroxycamptothecin for injection; Y, vehicle control group; d0, before administration; d3, the third day after the first administration; d6, the 6th day after the first administration; d9, the 9th day after the first administration; d12, the 12th day after the first administration; d15, the 15th day after the first administration; d21, the 7th day after the last administration; *$p < 0.05$, **$p < 0.01$, $^\Delta p < 0.001$.

The results in Table 2 show that after 3 and 6 continuous administrations, each administration group has no statistical significance as compared with the vehicle control group, with all p value >0.05.

The test results show that, after 6 continuous administrations, the proliferation of tumor cells in the administration groups administered with various doses of rhCNB for injection and the positive control administration groups is well controlled, but there is no statistical significance as compared with the vehicle control group, with all p value >0.05.

The test results show that, after administration for 9 consecutive days, the administration groups G, Z, D and DZ of rhCNB for injection and the positive control administration groups SD and X all have significant statistical significance in the control of tumor cell proliferation as compared with the vehicle control group, with p<0.01, and the positive control administration group B shows statistical significance as compared with the vehicle control group, with p<0.05.

The test results show that, after administration for 12 consecutive days and 15 consecutive days, the administration groups G, Z, D, and DZ of rhCNB for injection and the positive control administration groups B, SD and X all have extremely significant differences in the control of tumor cell proliferation as compared with the vehicle control group, with p<0.001.

The test results show that, on the 7th day after the last administration, the administration groups G, Z, D and DZ of rhCNB for injection and the positive control administration group B all have extremely significant differences in the control of tumor cell proliferation as compared with the vehicle control group, with p<0.001. The administration groups SD and X show significant differences, with p<0.01.

Figure 2:
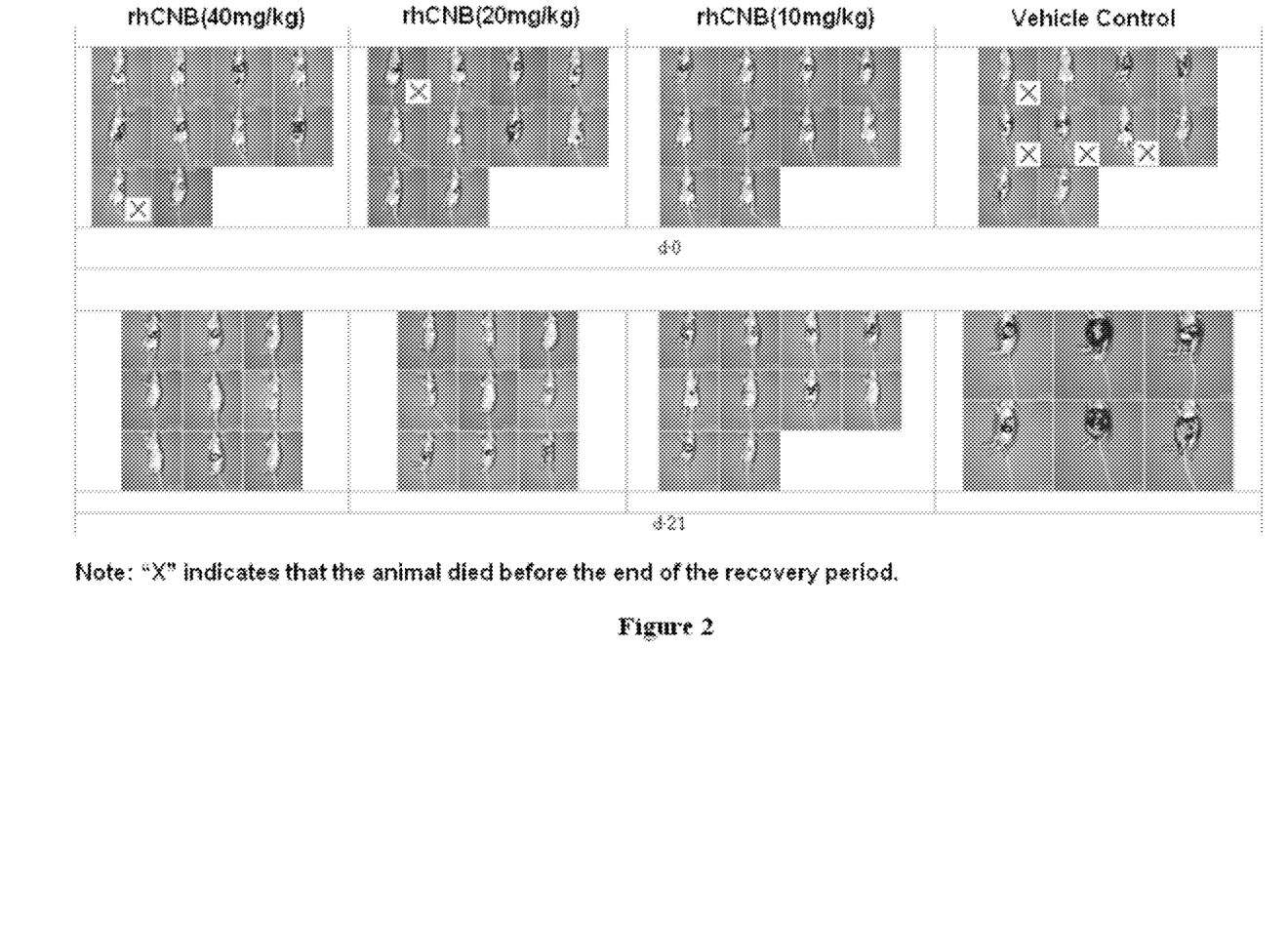
FIG. 2 shows the live imaging; wherein "X" indicates that the animal has died before the end of the recovery period.
Figure 3:
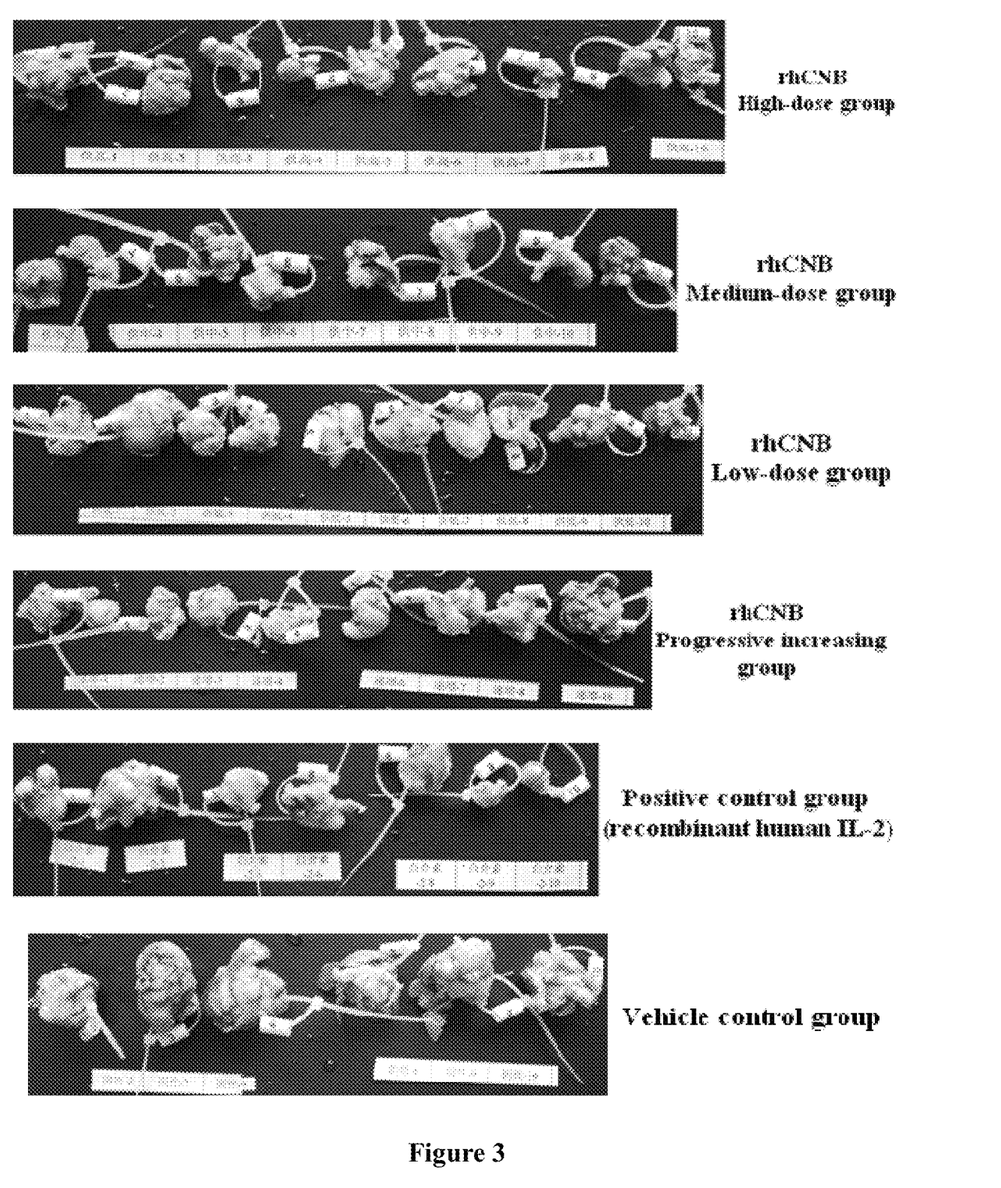
FIG. 3 shows a necropsy image.

It is noteworthy that during the experiment, there are animals for which the presence of tumor cells cannot be detected during different administration periods in the high-, medium- and low-dose groups of rhCNB for injection (see Table 3, FIG. 2, and FIG. 3). In combination with the results of necropsy, it was found that the transplantation tumors of these animals completely disappeared. After 9 to 12 continuous administrations, the test results show that, there is one animal, in which the tumor cannot be detected, in both the high- and low-dose groups; after 15 continuous administrations, there are 2 animals, in which the tumor cannot be detected, in the high-dose group, and one animal in the low-dose group; the test results show that on the 7th day after the last administration, there are 4 animals, in which the tumor cannot be detected, in the high-dose group, 2 animals in the medium-dose group, and one animal in the low-dose group.

In addition, some animals died during the experiment. In combination with the experimental results of carcinoma in situ of liver cancer, it is preliminarily believed that the death of the animals in the administration group of cisplatin for injection is mainly due to drug toxicity, and the death of the animals in the each remaining administration group is mainly due to the serious effect of gastric cancer on their food intake.

TABLE 3

Number of animals in which tumor is not detectable and not observed in each experimental group

| Group | d0 | d3 | d6 | d9 | d12 | d15 | recovery period d7 |
|---|---|---|---|---|---|---|---|
| G | 0 | 0 | 0 | 1 | 1 | 2 | 4 |
| Z | 0 | 0 | 0 | 0 | 0 | 0 | 2 |
| D | 0 | 0 | 0 | 1 | 1 | 1 | 1 |
| DZ | 0 | 0 | 0 | 0 | 0 | 0 | 0 |
| SG | 0 | 0 | 0 | 0 | 0 | 0 | 0 |
| SD | 0 | 0 | 0 | 0 | 0 | 0 | 0 |

TABLE 3-continued

Number of animals in which tumor is not detectable and not observed in each experimental group

| Group | d0 | d3 | d6 | d9 | d12 | d15 | recovery period d7 |
|---|---|---|---|---|---|---|---|
| B | 0 | 0 | 0 | 0 | 0 | 0 | 0 |
| X | 0 | 0 | 0 | 0 | 0 | 0 | 0 |
| Y | 0 | 0 | 0 | 0 | 0 | 0 | 0 |

3 Conclusions

In the therapeutic effect of rhCNB for injection on BALB/c nude mice bearing transplantation tumor of human gastric cancer cell MGC-803 carcinoma in situ, after 3 to 6 continuous administrations, the administration groups with doses of 10 mg/kg, 20 mg/kg, and 40 mg/kg of rhCNB for injection all have a certain inhibiting effect on the growth of human gastric cancer cell MGC-803 solid tumor, but there is no significant statistical difference (p>0.05) as compared with the vehicle control group. The test results show that, during the subsequent administrations, the effect of the high-, medium-, low-dose groups and progressively increasing-dose group of rhCNB for injection on the inhibition of tumor cell proliferation shows highly significant difference (p<0.001) as compared with the vehicle control group, and the effect is comparable to that of the positive control groups of the recombinant human interleukin-2 for injection, hydroxycamptothecin, and cisplatin for injection. The test results show that, on the 7th day after the last administration, the effect of the high-, medium-, low-dose groups and progressively increasing dose group of rhCNB for injection on the inhibition of tumor cell proliferation still show extremely significant difference (p<0.001) as compared with the vehicle control group, and the therapeutic effect on tumor is superior to that of positive control groups. It is suggested that 7 days after drug withdrawal, the high-, medium-, low- and progressively increasing dose administration groups of rhCNB for injection each and the control groups still show a good inhibiting effect on the proliferation of tumor cells (p<0.001).

Taking the above analysis together, the following conclusions can be drawn preliminarily:

When use rhCNB for injection to treat BALB/c nude mice bearing transplantation tumor of human gastric cancer cell MGC-803 carcinoma in situ, the tumor is effectively treated after 6 continuous administrations (as compared with the vehicle control group, p<0.05), and can be effectively controlled throughout the administration. One week after the drug withdrawal, there is still a continuous and effective therapeutic effect on tumors (as compared with the vehicle control group, p<0.001), which is superior to the positive controls cisplatin for injection and hydroxycamptothecin for injection, and is comparable to the recombinant human interleukin-2 for injection.

The use of the recombinant human calcineurin B subunit provided by the present invention is described in detail above. Specific examples are used herein to elaborate the principle and embodiments of the present invention, and the above description of the examples is only for helping to understand the methods of the present invention and core idea thereof. It is to be noted that, for those skilled in the art, several improvements and modifications can also be made to the present invention without departing from the principle of the present invention, and such improvements and modifications fall within the protection scope of the claims of the present invention as well.

What is claimed is:

1. A method for treating a cancer in a subject, comprising administering recombinant human Calcineurin subunit B (rhCNB) to the subject, wherein the cancer is gastric cancer.

2. The method according to claim 1, wherein the treating is killing or inhibiting the proliferation of the gastric cancer cells.

3. The method according to claim 1, wherein the treating is improving the survival of the subject.

4. The method according to claim 1, wherein the cancer is derived from human gastric cancer cell MGC-803.

5. The method according to claim 1, wherein the cancer is metastatic cancer derived from human gastric cancer cell MGC-803 carcinoma in situ.

6. The method according to claim 1, wherein the rhCNB is administered at a dose of not less than 10 mg/kg.

7. The method according to claim 1 or 2, wherein the rhCNB is administered at a dose between 10 mg/kg and 160 mg/kg.

8. The method according to claim 1, wherein the rhCNB is administered at a concentration between 0.5 mg/mL and 2 mg/mL.

9. The method according to claim 1, wherein the rhCNB is administered via intravenous injection once daily for 15 consecutive days, at a dose of 10, 20, 40 mg/kg or at a first dose of 10 mg/kg, followed by doubling the preceding dose every 3 days, which are 20 mg/kg, 40 mg/kg, 80 mg/kg, and 160 mg/kg successively.

* * * * *